United States Patent [19]

Hansen, deceased et al.

[11] Patent Number: 4,905,450
[45] Date of Patent: Mar. 6, 1990

[54] PROCESS AND APPARATUS FOR FILLING AND SEALING A CONTAINER, AND A CONTAINER MADE THEREBY

[76] Inventors: Gerhard Hansen, deceased, late of Sulzbach-Laufen; by Heidrun Hansen, legal representative, Heerstrasse 20, 7166 Sulzbach-Laufen 2, both of Fed. Rep. of Germany

[21] Appl. No.: 208,491

[22] Filed: Jun. 20, 1988

[30] Foreign Application Priority Data

Jun. 27, 1987 [DE] Fed. Rep. of Germany ....... 3721308

[51] Int. Cl.⁴ ................. B65B 31/00; B65B 3/00; B65B 3/18
[52] U.S. Cl. .............................. 53/410; 53/434; 53/453; 53/469; 53/479
[58] Field of Search ............. 53/434, 410, 412, 479, 53/469, 486, 489, 453, 560, 561

[56] References Cited

U.S. PATENT DOCUMENTS

| | | | |
|---|---|---|---|
| 3,251,915 | 5/1966 | Pechthold | 53/561 X |
| 3,381,441 | 5/1968 | Condo, Jr. et al. | 53/551 X |
| 3,457,694 | 7/1969 | Tatibana | 53/289 UX |
| 3,625,786 | 12/1971 | Pearson et al. | 53/289 X |
| 3,690,803 | 9/1972 | Pechtold et al. | 53/561 X |
| 4,338,765 | 7/1982 | Ohmori et al. | 53/289 X |

FOREIGN PATENT DOCUMENTS

| | | |
|---|---|---|
| 1931710 | 1/1971 | Fed. Rep. of Germany . |
| 2140505 | 3/1972 | Fed. Rep. of Germany . |
| 3005931 | 12/1982 | Fed. Rep. of Germany . |

*Primary Examiner*—Horace M. Culver
*Attorney, Agent, or Firm*—Roylance, Abrams, Berdo & Goodman

[57] ABSTRACT

To minimize the air volume present in a container following heat sealing, the dimensions of the flowthrough passage of the filling connection are decreased in a first heat sealing operation. Then, the container is elastically deformed by a punch to such an extent that the liquid content level rises up inside the filling connection. Finally, in a second heat sealing operation, the end segment of the now funnel-shaped flowthrough passage of the filling connection is heat sealed such that it is totally sealed without pores.

5 Claims, 2 Drawing Sheets

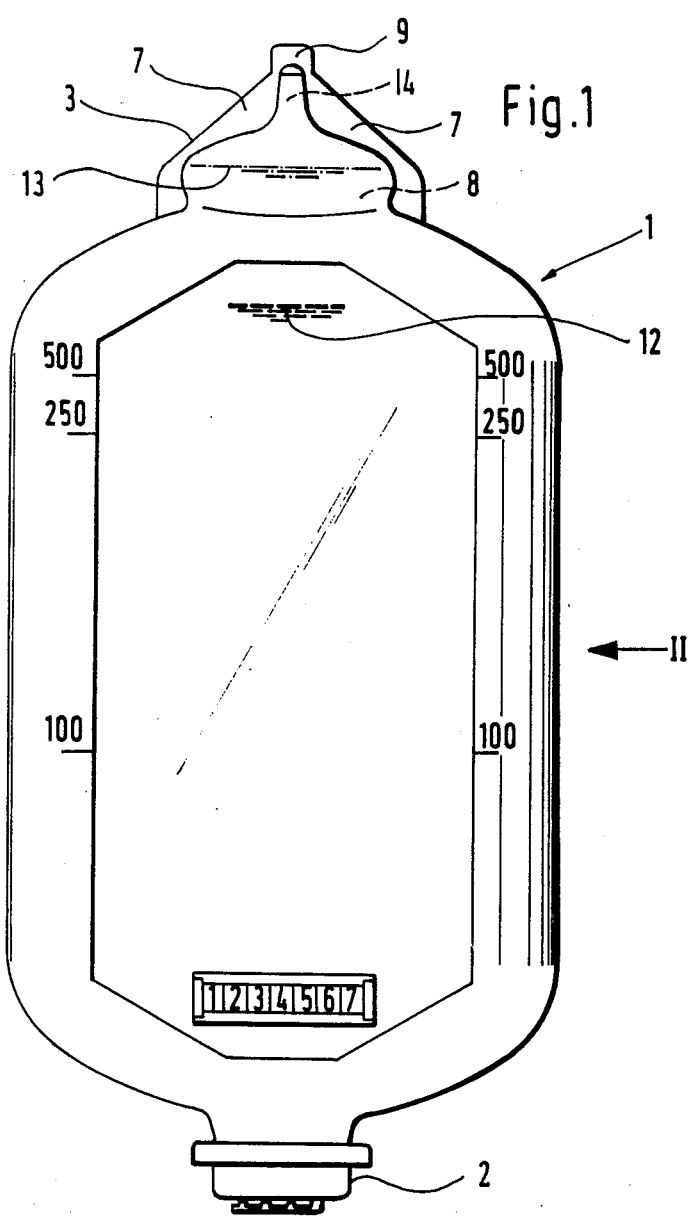

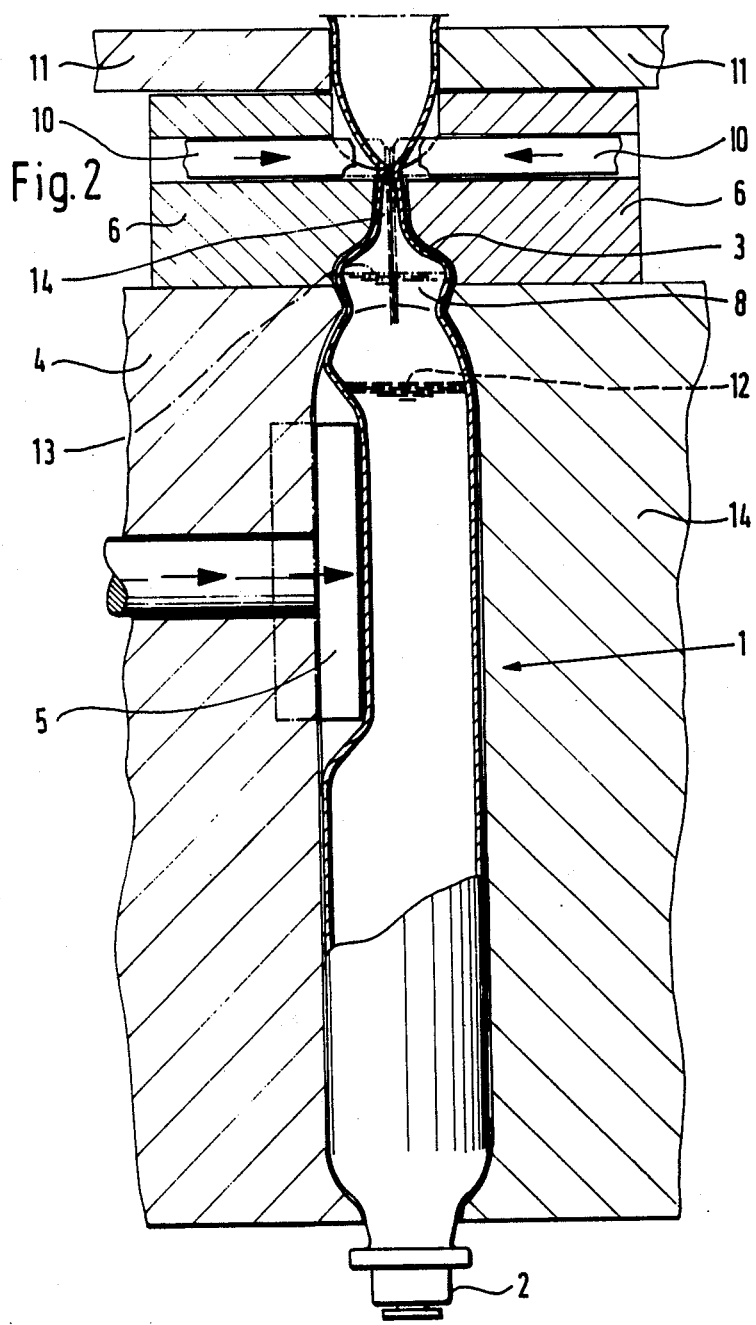

PROCESS AND APPARATUS FOR FILLING AND SEALING A CONTAINER, AND A CONTAINER MADE THEREBY

FIELD OF THE INVENTION

The present invention relates to a process and apparatus for filling and subsequently totally heat sealing a container which is elastically deformable, at least in part of its body, and to the container filled and sealed by that process and apparatus. The container is formed with a filling connection having a transverse cross section smaller than that of the container. The filling connection is pressed flat and heat sealed at least in its border area following the filling.

BACKGROUND OF THE INVENTION

With known processes and apparatus for filling and heat sealing a container, a relatively large volume of air remains in the container following its filling and heat sealing. If the container is a sack, bag or pouch (hereinafter "pouch") containing a liquid infusion, a pressure infusion cannot be performed although it would be desirable in emergencies. As a result of the pressure built up resulting from the pressure infusion, the air contained in the conventional pouch could be injected into the blood. This remaining volume of air is relatively large so that the contents level will be located at a sufficiently great distance from the heat sealing point at which the filling connection is attached.

The known process disclosed in German Patent No. A-19 31 710 is concerned with this disadvantage. Following the filling of the liquid contents into the container, the flowthrough passage of the filling connection is reduced in a first heat sealing operation. Air or some other gas is then pressed into the container producing an excess pressure. Subsequently, the filling connection is closed in a second heat sealing operation. The volume of air or gas contained in the container is also increased in this system.

SUMMARY OF THE INVENTION

An object of the present invention is to provide an improved process and apparatus for filling and heat sealing an elastically deformable container wherein the volume of air remaining in the filled and sealed container can be considerably decreased.

Another object of the present invention is to provide an elastically deformable container which is filled and heat sealed and which contains a minimum amount of air.

The foregoing objects are obtained by a process for filling and sealing an at least partially elastically deformable container of heat sealable material, comprising the steps of filling an elastically deformable container through an open end thereof to a first level of contents, in a first heat sealing step forming a filling connection at the container open end having a flow passage with transverse cross-sectional dimensions smaller than a body portion of the container by pressing flat and heat sealing a border zone of the container open end after filling, the passage remaining open at a distal end thereof, and in a second heat sealing step closing and sealing the distal end of the passage. Between the first and second heat sealing steps, the contents are raised to a higher, second level inside the filling connection of the container by elastically deforming the container.

Since the volume of space in the container remaining free is reduced as a result of the reduction of the flow-through passage in the filling connection in the first heat sealing step, a relatively slight deformation of the container body is sufficient to raise the filling level or top surface of the contents in order to press out the greatest portion of the air still remaining in the container body and in the filling connection. When the remaining passage opening is heat sealed in the second heat sealing step, then despite the distance which must be present between the filling level and this heat sealing point of the second heat sealing step, the remaining volume still containing air is sufficiently small that the air in that space no longer creates any disturbance in the procedure. By using the process according to the present invention to form a pouch filled with a liquid infusion, such pouch can be used in a pressure infusion.

The foregoing objects are also obtained by an apparatus for heat sealing a filled container which is at least partially elastically deformable, comprising holding means for supporting the container, heat sealing means for forming a filling connection at and sealing an open end of the container, and displaceable means, mounted adjacent the holding means, for moving against and applying pressure to the container. The heat sealing means includes first and second pairs dies movably mounted above the holding means. The first pair of dies having mating sealing surface means for forming the filling connection having a flow passage therethrough with transverse cross-sectional dimensions smaller than a body portion of the container and with an open distal end. The first dies terminate at a distance from the open distal end. The second pair of dies has mating sealing surface means, extending as far as the sealing surface means of the first pair of dies and the distal open end and connected with the sealing surface means of the first pair of dies, for sealing the open distal end closed.

Together with its holder, this apparatus can form a container of plastic material by the blow molding process. Known forms of container blow molding apparatus require, for this purpose, only a simple modification, manifested as a recess or section for the displaceable means. The displaceable means can be in the form of a punch, by means of which the wall of the container is temporarily deflected inward.

The foregoing objects are further obtained by a container, comprising a hollow body portion with at least one elastically deformable part, an internal chamber for contents, and a totally pore-sealed and heat sealed filling connection at one end of the body portion. A flow passage extends through the filling connection. The flow passage has an open distal end and an opposite near end opening in the chamber, and is considerably smaller in transverse cross section at the open distal end than at the near end.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure:

FIG. 1 is a side elevational view of a filled and sealed container according to the present invention; and FIG. 2 is a side elevational view in section of an apparatus for forming, filling and heat sealing the container of FIG. 1 according to the present invention.

DETAILED DESCRIPTION OF PREFERRED EMBODIMENT

An elastically deformable plastic pouch 1 formed by the blow molding process and intended to receive a liquid infusion is illustrated in FIGS. 1 and 2. As traditional with such pouches, the pouch or container has a flat shape. A discharge connection 2, located at the bottom during the filling step, is constructed in a known manner. A filling connection 3 is tip-stretched in a known manner onto the top end of pouch 1 and projects upwardly during the filling. Connection 3 in this invention must be of considerable length.

Pouch 1 is manufactured by the blow molding process from a tube introduced into a matrix body or mold 4. The hollow space or cavity of matrix body 4 has dimensions corresponding to the shape of pouch 1, as shown in FIG. 2.

In the area forming one of the side surfaces of pouch 1, matrix body has a recess receiving a displacement punch 5. This displacement punch 5 has a contour coinciding with the shape of the recess and engages, on its entire periphery, without play, at least for the most part, the bordering wall of the recess. The punch work surface faces the hollow space formed by matrix body and is flush with the inside surface of matrix body 4, when displacement punch 5 is found in its nonoperational or retracted position. In the retracted position, the punch work surface forms a part of the contact or mold surface for pouch 1.

The filling connection 3 projects over the top of matrix body 4. Two mating head dies 6 are mounted on top of matrix body 4 for movement relative to one another as parts of a heat sealing device to heat seal filling connection 3. The work surfaces of head dies 6 face one another and press the parison material forming the sides of filling connection 3 against each other only along an outside border area, so that a total heat sealing without pores occurs only in this area. Both of the heat sealed border zones 7 of the border area are produced by dies 6, as indicated in FIG. 1.

As shown in FIG. 1, the border zones 7 extend into the area connecting the filling connection with the body of pouch 1. From the pouch body, the sealed border zones first extend parallel to each other, and then uniformly approach one another up to a very close distance from each other. The area 8, between sealed border zones 7, of the filling connection is not heat sealed by head dies 6, and thus has the form of a funnel following the first heat sealing procedural step performed by dies 6.

The flowthrough passage of filling connection 3 narrows considerably from a first segment terminating or opening into the inside chamber of pouch 1. An end segment 14 of the filling connection passage is connected to the first segment and corresponds to the outlet tube of the funnel. The end segment has a very small transverse cross-sectional diameter. The flowthrough passage continues to narrow, but only very slightly, toward the passage opening 9 in the end segment. The passage opening is totally sealed without pores when in heat sealed state upon completion of the container or pouch.

The work surfaces of head dies 6 terminate a small distance below passage opening 9. Each of the two head dies 6 has one recess. Two additional dies 10 are slidably mounted in the recesses of the head dies. The direction of thrust of additional die members 10 is identical to that of head dies 6 for the purpose of heat sealing passage opening 9 so that the pouch is totally sealed without pores. These work surfaces of additional dies 10 are configured so that the material of filling connection 3 is pressed together holohedrally, i.e., uniformly around its entire surface, between the additional dies. Dies 10 can be heated with a heating device (not shown). If a foaming liquid fills the pouch and foam should then get as far up as dies 10, a total heat sealing without pores is still attained by heating dies 10.

Above their work surfaces, the two head dies 6 together define a space which widens upwardly. One end portion of the tube or parison from which the pouch 1 is produced is located in that space. Wedging dies 11 arranged above head dies 6 hold the end portion of the tube in position by engaging the wedging die work surfaces facing toward each other on the tube. Suction passages open on the wedging die work surfaces to retain the tube end portion.

Following the production of pouch or container 1 in matrix body 4 by the blow molding process, and after the container is finally filled to a level shown in FIGS. 1 and 2 by line 12 and one piece lies far below the bottom end of filling connection 3, the two head dies 6 are brought together. Border zones 7 are thus heat sealed together, forming filling connection 3 into the funnel-like shape shown in FIGS. 1 and 2. Of the entire flowthrough passage of filling connection 3, only end segment 14 forming the opening 9 still remains open.

One side wall of pouch 1 is then deflected inwardly by displacement punch 5. The liquid level is raised from line 12 by the deflection approximately to a line 13 within filling connection 3 as shown in FIGS. 1 and 2. This line lies approximately at the site where the flowthrough passage of the filling connection begins to narrow. With raising of the liquid level as far as line 13, the major portion of the air which was first in pouch 1 and filling connection 3 and is still present in pouch 1 and connection 3 is forced out through pouch end segment 14. At this time with the pouch deflected by punch 5, end segment 14 is heat sealed in a manner that is totally sealed without pores by additional dies 10. The distance of the liquid level from this sealed point is still sufficiently great. However, the volume of air still present in filling connection 3 is negligeably small, because the transverse cross-sectional area of the flowthrough passage of filling connection 3 has already been greatly reduced in the first heat sealing step by head dies 6.

During the heat sealing of end segment 14, the upper projecting part of the tube is sheared off by the action of additional dies 10. Also, during the second heat sealing step, displacement punch 5 is drawn back to its retracted or inactive position. The inward deflection of pouch 1 is then obviated, and pouch 1 can then be removed from matrix body 4 in the form represented in FIG. 1.

While a particular embodiment has been chosen to illustrate the invention, it will be understood by those skilled in the art that various changes and modifications can be made therein without departing from the scope of the invention as defined in the appended claims.

What is claimed is:

1. A process for filling and sealing an at least partially elastically deformable container of heat sealable material, comprising the steps of:

filling an elastically deformable container through an open end thereof to a first level of contents;

in a first heat sealing step, forming a filling connection at the container open end having a flow passage with transverse cross-sectional dimensions smaller than a body portion of the container by pressing flat and heat sealing a border zone of the container open end after filling, the passage remaining open at a distal end thereof;

in a second heat sealing step, closing and sealing the distal end of the passage; and between the first and second heat sealing steps, raising the contents to a higher, second level inside the filling connection of the container by elastically deforming the container.

2. A process according to claim 1 wherein, in the first sealing step, the passage is formed with transverse cross-sectional dimensions in an end segment thereof adjacent the open distal end which are significantly smaller than transverse cross section dimensions of another segment of the passage between the end segment and an inside space of the container.

3. A process according to claim 2 wherein, in the first sealing step, the passage is formed in the other segment with transverse cross-sectional dimensions diminishing progressively in a direction away from an opposite closed end of the container and to have a funnel shape, and is formed in the end segment of the passage with transverse cross-sectional dimensions diminishing less progressively.

4. A process according to claim 1 wherein a projecting part of the filled container is separated from heat-sealed portions thereof.

5. A process according to claim 1 wherein said second heat sealing step is performed at a level spaced above said second level.

* * * * *